United States Patent
Street et al.

(10) Patent No.: US 10,466,193 B2
(45) Date of Patent: Nov. 5, 2019

(54) PRINTED GAS SENSOR

(71) Applicant: Palo Alto Research Center Incorporated, Palo Alto, CA (US)

(72) Inventors: Robert A. Street, Palo Alto, CA (US);
David Eric Schwartz, San Carlos, CA (US); Ping Mei, San Jose, CA (US);
Brent S. Krusor, Fremont, CA (US);
Jonathan Rivnay, Chicago, IL (US);
Yong Zhang, Millbrae, CA (US);
Gregory L. Whiting, Menlo Park, CA (US); Sivkheng Kor, San Jose, CA (US); Steven E. Ready, Los Altos, CA (US)

(73) Assignee: PALO ALTO RESEARCH CENTER INCORPORATED, Palo Alto, CA (US)

( * ) Notice: Subject to any disclaimer, the term of this patent is extended or adjusted under 35 U.S.C. 154(b) by 338 days.

(21) Appl. No.: 15/446,448

(22) Filed: Mar. 1, 2017

(65) Prior Publication Data
US 2018/0252659 A1    Sep. 6, 2018

(51) Int. Cl.
*G01N 27/12* (2006.01)
*G01N 33/00* (2006.01)

(52) U.S. Cl.
CPC ....... *G01N 27/122* (2013.01); *G01N 33/0036* (2013.01)

(58) Field of Classification Search
CPC ...... G01N 1/00; G01N 2201/00; H01L 21/00; H01L 2221/00
See application file for complete search history.

(56) References Cited

U.S. PATENT DOCUMENTS

| | | | |
|---|---|---|---|
| 8,481,994 B2 | 7/2013 | Burroughes et al. | |
| 8,889,473 B2 | 11/2014 | Benwadith et al. | |
| 9,735,380 B2 | 8/2017 | Koizumi et al. | |
| 9,997,709 B2 | 6/2018 | Noh | |
| 2006/0055392 A1* | 3/2006 | Passmore | B82Y 15/00 324/71.1 |
| 2007/0040170 A1* | 2/2007 | Cain | B82Y 10/00 257/57 |
| 2011/0290296 A1* | 12/2011 | Daniel | H01L 31/042 136/244 |
| 2011/0290304 A1* | 12/2011 | Daniel | H01L 31/03926 136/251 |
| 2012/0297864 A1* | 11/2012 | Abawi | G01D 3/028 73/112.01 |
| 2014/0311905 A1* | 10/2014 | Stetter | B01J 31/06 204/424 |

OTHER PUBLICATIONS

Colin Reese et al. "Organic Thin Film Transistors", Materials Today, vol. 7, Iss. 9, Sep. 2004, pp. 20-27; https://www.sciencedirect.com/science/article/pii/S1369702104003980 accessed Dec. 10, 2018.

* cited by examiner

*Primary Examiner* — Jermele M Hollington
*Assistant Examiner* — Temilade S Rhodes-Vivour
(74) *Attorney, Agent, or Firm* — Fay Sharpe LLP

(57) ABSTRACT

A printed resistive gas detector configuration that is simple, inexpensive and compact, fabricated for incorporation into an electronic device, such as an electronic computing and/or communication device, the printed resistive gas detector configuration designed to continuously monitor for predetermined types of gasses. The printed resistive gas detector configuration manufactured by the use of printing technology to print on a flexible substrate.

18 Claims, 13 Drawing Sheets

PRINTED GAS SENSOR

BACKGROUND

It is known that operation of chemical, physical or electronic systems may produce potentially dangerous gasses, where such gasses may be toxic and/or explosive. Additionally, while other gasses may not be dangerous there may still be valuable reasons to monitor their concentrations. It is therefore considered desirable to provide a simple, flexible, inexpensive and compact gas sensor.

BRIEF DESCRIPTION

A system is set forth including a gas sensor having a flexible substrate carrying a printed resistive gas detection arrangement comprised of a resistive gas sensor material which alters its resistance characteristics upon coming into contact with a gas to be sensed. The gas sensor further includes a printed bias input line arrangement configured to supply a bias voltage to the printed resistive gas detection arrangement, a printed load resistive element positioned to form a voltage divider network with the printed resistive gas detection arrangement, a printed supply line configured to provide a supply voltage in accordance with the voltage divider, a printed gain stage configured to receive the supply voltage of the voltage divider, and a printed gain stage bias input line arrangement configured to supply a bias voltage to the gain stage. Also included is a printed output line in operational association with an output portion of the printed gain stage.

Another aspect includes a gas presence indicator, configured to indicate a presence of a sensed gas.

Another aspect includes an output stage configured to couple output of the gain stage to a gas presence indicator.

Another aspect includes (i) a wireless transmitter configured to receive output from at least one of the printed gain stage and an output stage associated with the printed gain stage, and (ii) a gas presence indicator having a wireless receiver to receive a gas presence signal from the wireless transmitter.

Another aspect includes having the printed gain stage being at least one of a single inverter or a series of connected inverters.

Another aspect includes the printed gain stage being at least one of a feedback latch and a half latch.

Another aspect includes where at least some of the printed portions are part of a printed conductive layer formed by use of at least one of a metal material, a carbon material, and a conductive polymer material.

Another aspect includes the printed resistive gas detection arrangement configured with carbon nanotubes, where the carbon nanotubes are at least one of functionalized carbon nanotubes, carbon nanotubes coated with polymers, and carbon nanotubes are decorated with nanoparticles.

Another aspect includes having supply voltages supplied to the printed gain stage and the printed resistive gas detection arrangement calibrated by software control operations and a feedback circuit.

Another aspect includes having the printed conductive layer, the printed resistive gas detection arrangement, the printed bias input line, the printed load resistive element, the printed supply line, the printed gain stage, and the printed output line formed to be flexible and compact.

Another aspect includes the printed gas detection arrangement having more than a single printed gas detector, where each printed gas detector of the printed gas detection arrangement configured to sense a different gas.

Another aspect includes the flexible substrate, the printed conductive layer, the printed resistive gas detection arrangement, the printed bias input line, the printed load resistive element, the printed supply line, the printed gain stage, and the printed output line arranged as part of at least one of an electronic computing device and/or an electronic communication device, and where the printed output line is in operational association with a visual display or speaker of the electronic computing device and/or the electronic communication device.

Further set forth is a system which includes a gas sensor which includes a flexible substrate carrying a number of elements including a flexible conductive layer formed in a predetermined pattern. A printed resistive gas sensor configuration carried at least partially on the conductive layer which includes (i) a printed resistive gas detection arrangement including a resistive gas sensor material designed to alter its resistance characteristics upon coming into contact with a gas to be sensed, the printed resistive gas detection arrangement operationally associated with at least a portion of the printed gas detection arrangement printed onto a portion of the conductive layer and including a bias voltage input area, (ii) a printed bias input line arrangement, of the conductive layer, configured to supply a bias voltage to the bias voltage input area of the printed resistive gas detection arrangement, (iii) a printed load resistive element positioned to form a voltage divider network with the printed resistive gas detection arrangement, wherein at least a portion of the printed load resistive element is printed onto a portion of the conductive layer and including to a ground line of the conductive layer, (iv) a printed supply line, of the conductive layer, configured to supply a voltage in accordance with the voltage divider. Also included is a printed gain stage including an output portion and an input portion and configured to receive the supply voltage from the voltage divider at its input portion, and configured for its output portion to be in operational association with an output line of the conductive layer.

Another aspect includes the substrate, the printed conductive layer, the printed resistive gas detection arrangement, the printed bias input line, the printed load resistive element, the printed supply line, the printed gain stage, and the printed output line are arranged as part of at least one of an electronic computing device and an electronic communication device, and wherein the printed output line is in operational association with a visual display or speaker of the at least electronic computing device and electronic communication device.

Further set forth is a method for forming a system including a gas sensor, the method includes providing a flexible substrate. Thereafter a number of steps are provided, including printing a resistive gas detection arrangement including a resistive gas sensor material designed to alter its resistance characteristics upon coming into contact with a gas to be sensed; printing a bias input line arrangement configured to supply a bias voltage to the printed resistive gas detection arrangement; printing a load resistive element positioned to form a voltage divider network with the printed resistive gas detection arrangement; printing a supply line configured to provide a supply voltage in accordance with the voltage divider; printing a gain stage to receive the supply voltage of the voltage divider; printing a gain stage bias input line arrangement configured to supply a bias voltage to the gain stage; and printing an output line in operational association with the output portion of the printed gain stage.

Another aspect includes having the printing steps are additive processes and where only material that is needed to print the gas sensor is deposited.

Another aspect includes wherein the printing of the gain stage includes printing a thin film transistor which includes printing a surface work function modifier on at least certain electrodes and processing the surface work function modifier to modify the surface work function of the certain electrodes, and wherein the printed surface work function modifier is printed substantially only on surfaces of the certain electrodes.

Another aspect includes having the printing steps undertaken using a printing system having multiple print heads, where a plurality of materials are deposited by the same printing system, and where the printing materials include at least resistive material, semiconductor material, interface layer material, conductive material.

DETAILED DESCRIPTION

The present disclosure describes systems and methods for a gas sensor that is simple, compact and inexpensive to fabricate. It is designed or configured for incorporation into electronic circuits and/or devices to monitor for such gases. The circuits and/or devices including an electronic communication device and/or an electronic computing device such as but not limited to personal mobile electronic devices such as a smart phone, cell phone, desk top computer, laptop, tablet, or other electronic device, in order to continuously monitor for dangerous gasses and/or other gasses of interest. Such gases including but not limited to carbon monoxide (CO), ammonia ($NH_3$), nitric oxide (NO) and other common pollutants, volatile organic compounds, as well as non-toxic gasses such as carbon dioxide ($CO_2$) and water vapor. The gas sensor is fabricated by use of a printing system which prints the gas detector on a substrate such as but not limited to a flexible substrate.

Figure 1:
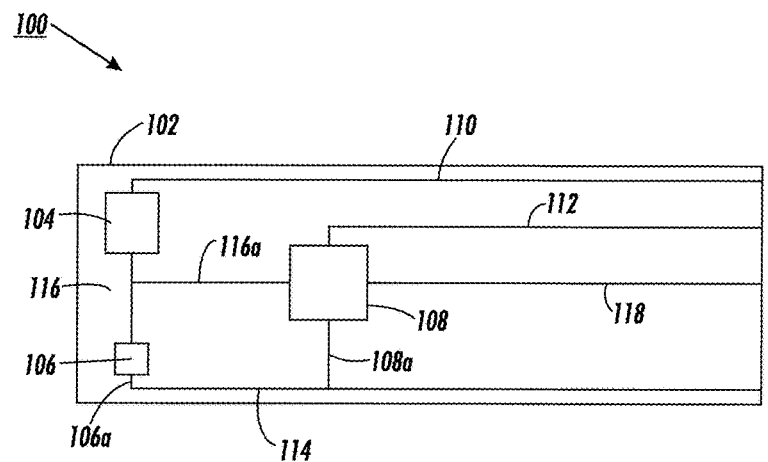
FIG. 1 is a diagram illustrating concepts of the present disclosure.

With attention to FIG. 1, depicted is a block diagram of a printed gas sensor circuit 100 according to the teachings of the present application. Provided is a flexible substrate 102 on which is printed components of the printed gas sensor 100. In particular, printed on flexible substrate 102 are a printed gas detector (sensor) arrangement 104, a printed load resistance 106, and a printed gain stage 108. A printed bias input line arrangement 110 associated with the gas sensor arrangement 104, and a printed gain stage bias input line arrangement 112 associated with printed gain stage 108 are illustrated. Printed load resistance 106 includes a printed ground connection line 114 (which provides a connection point for load resistor 106 via load ground line 106a, and gain stage 108 via gain stage ground line 108a—when required). The printed gas sensor arrangement 104 and the printed load resistance 106 are connected in a form of a voltage divider 116 with a printed supply line 116a. Finally, an output signal line 118 is shown associated with printed gain stage 108. The printed gas detector (sensor) arrangement 104 may be a resistive gas detector (sensor).

In operation, when a predetermined gas (e.g., carbon monoxide or other gas) is sensed by printed gas detector (sensor) arrangement 104, the resistance of the gas detector (sensor) arrangement 104 is altered, thereby altering the output voltage on printed supply line 116a. This alters the voltage input to the gain stage 108. The gas sensor 100 is designed to then provide an output signal on output signal line 118. When a predetermined concentration of gas is sensed by printed gas detector (sensor) arrangement 104, it will result in a signal of appropriate strength on output signal line 118 to cause a signal indicator or gas presence indicator to be triggered. These concepts will be described in more detail below. FIG. 1 also shows that the various supply lines such as 110, 112, are accessible by power supplies, and with ground line 114 accessible to a ground.

Figure 2:
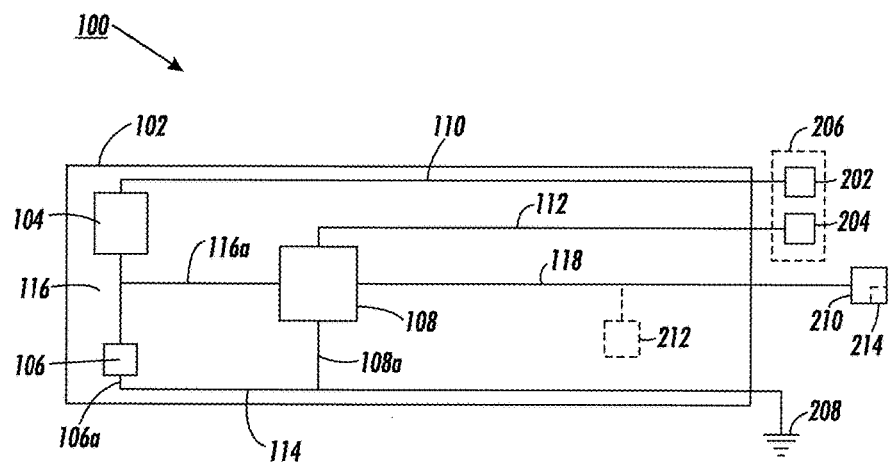
FIG. 2 is a diagram illustrating further concepts of the present disclosure.

Turning to FIG. 2, the gas sensor 100 is now shown wherein the previously discussed printed bias supply lines 110, 112, printed output signal line 118, and printed ground 114 are shown connected to off substrate elements. More specifically, the bias supply lines 110 and 112 are operationally associated or connected to power supply components 202 and 204. It is understood that while these are shown as individual power supply components, the dotted line 206 emphasizes that they may be part of a single power supply and the power supply components 202, 204 may be voltage dividers or controllers that can provide the same or different bias voltages to the gas sensor arrangement 104 and the gain stage 108. The ground line 114 is illustrated to be grounded at location 208 off of the flexible substrate 102. Finally, the output signal line 118 is operationally associated or connected to a gas presence indicator 210. It is understood this indicator 210 may be any of a number of electronic devices or components which provide an indication that the gas being monitored has been detected. In other words, when the gas detected by printed resistive gas detection (sensor) arrangement 104 is sensed at a certain predetermined concentration, the signal provided on output signal line 118 is of sufficient value to activate the gas presence indicator 210, thereby alerting a person, electronic device, etc. that the predetermined amount of gas concentration exists.

With continuing attention to FIG. 2 an alternative design feature (which can be employed in the other embodiments herein) provides for generating the gas presence output signal is a wireless readout, using a silicon IC attached to the flexible substrate, with printed connections to appropriate IC pads (contacts). For example, in an optional embodiment shown in FIG. 2, a wireless transmitter 212 is configured and positioned on substrate 102 to receive the output from the printed gain stage 108 (i.e., the direct line 118 to gas presence indicator 210 is removed and the dotted line 118a connects to wireless transmitter 212). Further the gas presence indicator is then optionally configured with a wireless receiver 214 to receive a gas presence signal from the wireless transmitter 212, and the signal is used to trigger the indicator 210.

Figure 3:
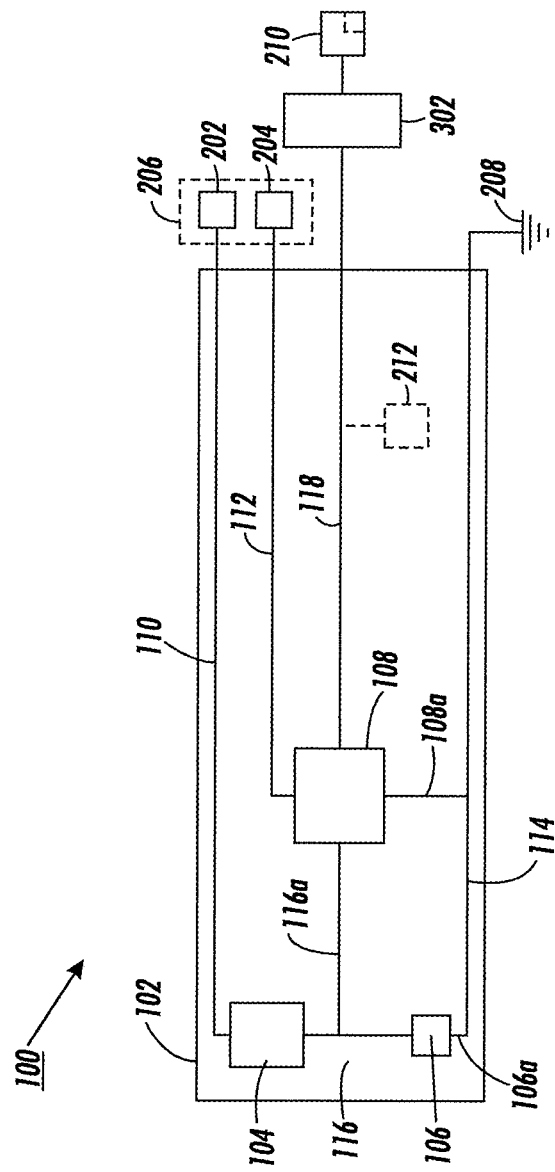
FIG. 3 is a diagram illustrating additional concepts of the present disclosure.

Turning to FIG. 3, again illustrated is the concept shown in FIGS. 1 and 2, but in this embodiment, it is noted that an output stage 302 is provided between the gas presence indicator 210 and the output signal line 118. In the embodiment of FIG. 3, it is understood that the output stage is an optional aspect. Its purpose in certain embodiments is to couple potentially relatively high-impedance output of a printed electronic circuit such as those shown on substrate 102 to the gas presence indicator 210. In particular, in certain embodiments, the indicator (e.g., in certain embodiments an LED) may require higher currents than are readily sourced by the printed gain stage (e.g., for example using TFTs) 108. More details about such a connection may be found in later discussions herein.

Figure 4:
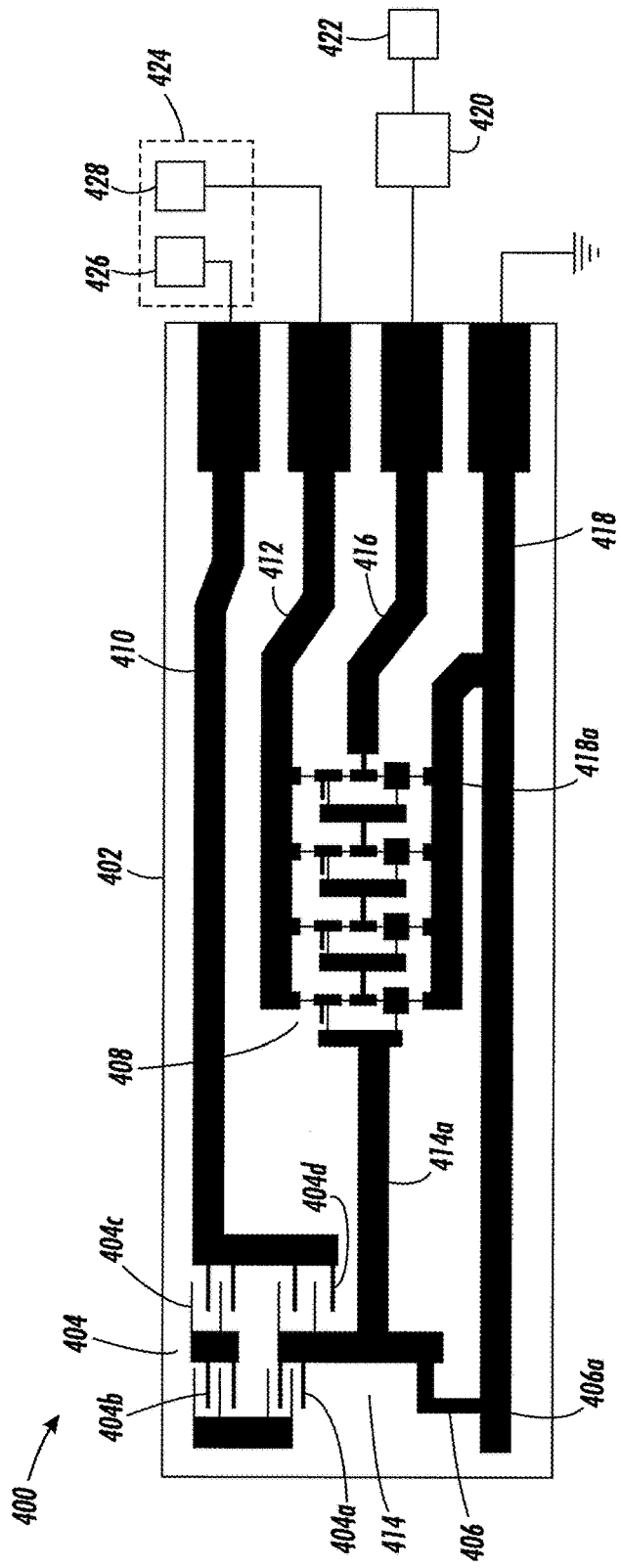
FIG. 4 is a diagram providing a more detailed view a system according to concepts of the present disclosure.

Turning to FIG. 4, depicted is a top view of a printed gas sensor 400 according to the concepts of the present application. FIG. 4 provides more detail for a particular embodiment of the printed gas sensor systems discussed in connection with FIGS. 1-3.

With continuing reference to FIG. 4, the printed gas sensor 400 is shown to include:

(1) A flexible substrate 402 which in certain embodiments is comprised of a plastic material such as but not limited to polyimide, polyethylene napthalate, or polyethylene terephthalate.

(2) A printed resistive gas detection (sensor) arrangement 404, comprised of a material such as but not limited to functionalized carbon nanotubes, which is printed from solution onto metal contacts. The material used to form the printed resistive gas detection arrangement 404 changes its resistive characteristics through absorption of gas on its surface which changes the charge state and thereby alters the resistance or conductivity of the material. It is also to be noted that in the embodiment of FIG. 4, the printed resistive gas detection arrangement 404 includes two distinct sensor configurations. The first sensor configuration consists of a chain of three sensors 404a, 404b, and 404c. The second sensor configuration consists of a single sensor 404d. In certain embodiments different sensor configurations may be used to sense different gasses (i.e., they will be printed using distinct gas detection material). The gas sensors may also be printed with electrodes having different sizes or designs which will alter the resistive characteristic of the sensor. The electrode design can be chosen to give a specific sensor resistance depending on the sensor material and provides flexibility in the circuit design and sensor performance optimization. Also, while the embodiment of FIG. 4 shows the sensors 404a, 404b, 404c, and 404d in an interdigitated arrangement, this is not a requirement and other designs may be used.

(3) A printed load resistive element (e.g., a printed load resistor) 406 comprised of carbon or other resistive material is printed between conductive material (e.g., metal contacts). The load resistive element 406 is positioned within the circuit to form a voltage divider 414 with the printed resistive gas detection arrangement 404. As will be discussed in greater detail below, one end of the load resistive element 406 is connected to a ground, while the other end is in operative association with the printed resistive gas detection arrangement 404.

(4) A gain stage 408 is embodied in FIG. 4 as a printed 4-stage inverter chain designed with p-channel and n-channel printed organic thin film transistors (TFT). In certain embodiments the TFTs are of top-gate configuration, with a PVDF-based gate dielectric, having high dielectric constant. Source, drain and gate contacts are printed metals, for example nano-particle silver, among others. The TFTs include interdigitated source and drain contacts to give high width-to-length (W/L) ratio in a compact area. The n-channel and p-channel devices are designed with different W/L to match the measured mobility of the semiconductors.

The printed TFTs also include a surface work function modification layer selectively printed on substantially only the metal source and drain contacts which acts to modify the surface energy levels of the source and drain electrodes, thereby minimizing contact resistance with the semiconductor material. The printed work function modification layer is used to match the metal (electrode) work function and the semiconductor work function, and may not be needed with some combinations of metal and semiconductor. The concept of printing the surface work function modifier "substantially only" on the surfaces of the source and drain electrodes is understood to mean that if any imprecise printing occurs where a small number of droplets are accidently deposited elsewhere, such as on the buffer layer of the substrate this is unintentional.

The gain stage 408 is configured to provide a significant amount of voltage gain, in other words the gain stage may receive a relatively small input voltage which will result in a much larger output voltage. While FIG. 4 shows the use of the four series inverter, it is to be understood the present concepts could also employ one, two, three or more inverters or another voltage gain circuit design, depending upon the particular implementation. If the implementation is to switch between ON or OFF, depending upon the amount of gas that has been sensed, the gain needs to be large enough to issue a gas presence signal once a predetermined concentration of gas has been detected, therefore the gain circuit would be designed to ensure a complete turn ON of an gas presence indicator once a trigger signal value is reached. On the other hand if the implementation is to provide a user with information as to particular levels of gas (e.g., 10, 100, 1000 parts per million . . . ) based on some predetermined scale, then the printed resistive gas detection arrangement 404 and the gain stage 408 are configured to provide a range of gas presence signals, correlated to a gas concentration percentage. In one design this may be accomplished by allowing a plurality of output signal levels (digital or analog) to be sent to a gas presence indicator that is calibrated to communicate the range of output signals to a user, another electronic device, etc. Also, while the gain stage 408 of FIG. 4 employs a TFT inverter chain, it is understood the gain stage may implemented in other forms such as but not limited to a transimpedance amplifier, feedback latch, and a half latch.

(5) Printed bias input line arrangement 410 (for the printed resistive gas detector arrangement 404), and printed bias input line arrangement 412 (for the gain stage 408), provide a path for applied bias voltages (Vdd) for the printed resistive gas detection (sensor) arrangement 404 and gain stage 408. The voltages can be the same or different, and may be supplied by the same or different voltage supply sources.

(6) Printed ground line 418 provides a ground connection for load resistance 406 (via load resistance ground line 406a), and gain stage 414 (via gain stage ground line 414a).

(7) Printed output line 416 provides a path for outputting of a gas presence signal.

The above components and elements forming the printed gas sensor circuit 400.

In certain embodiments the printed resistive gas sensor configuration (or printed gas sensor) 400 may have thickness in a range of approximately 10 to 500 microns (including the substrate) with a length in a range of approximately 2 to 10 cm, and a width in a range of approximately 1 to 5 cm.

In addition to the printed gas sensor 400, the embodiment of FIG. 4 also illustrates (similar to that shown in FIGS. 2 and 3):

(8) An output stage 420 which may be comprised of conventional electronics (e.g., a MOSFET switch, a Zener diode to set trigger voltage, a resistor to limit LED current). Depending upon the components employed, the output stage 418 may be an optional element.

(9) A gas presence indicator 422 triggered by the output voltage from the gain stage 408. In this embodiment the indicator is an LED, but many alternative choices are possible.

(10) A power supply arrangement 424 (with sub-components 426, 428).

In an ON-OFF switching embodiment the bias voltages and design are selected such that the gain stage inverter chain or other gain stage arrangement is close to its switching point in the absence of gas exposure. When exposed to gas, the sensor resistance changes and hence the input voltage to the gain stage (e.g., inverter chain) also changes. At a certain gas concentration, the input voltage change is large enough to give a sufficiently large change in the inverter output voltage to trigger the indicator.

Figure 5:
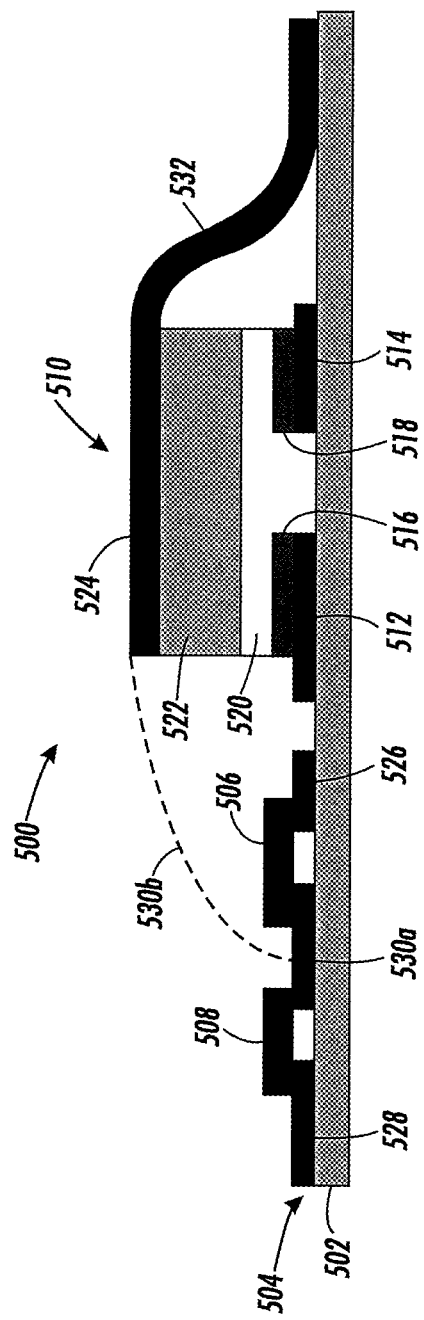
FIG. 5 is a cross-sectional view of portions of FIG. 4.

FIG. 5 is a cross-sectional view of a printed gas sensor 500, configured and manufactured in a manner similar to the foregoing teachings such that printed gas sensor 500 is a flexible sufficiently small sized device to be incorporated into electronic circuits and/or devices in order to monitor dangerous gasses and/or gasses otherwise of interest. In certain embodiments the electronic circuits/devices are in a form of an electronic computing and/or communication device such as but not limited to a cell phone, smart phone, laptop, desktop computer, tablet computer, or other such device including electronic circuitry that may expel or generate gases that may be of concern.

With continuing attention to sensor 500 of FIG. 5, while having similarities in construction and structure to sensor 400 of FIG. 4 various elements and/or structures do vary from that sensor construction. For example, the components of sensor 500 are illustrated as having an inverter TFT. Whereas FIG. 4 is depicted to include a string of inverter TFTs. It is however understood that sensor 500 can also be constructed with multiple TFTs as well. Similarly a resistive gas detection arrangement is shown as a single resistive gas detector (and not the resistive gas detection arrangement 404 of FIG. 4).

Turning to the structure of FIG. 5 provided is a substrate 502 on which various electrodes are formed by selective depositing of an electrode layer 504. Thereafter a resistive gas detection arrangement (e.g., a CNT gas detector) 506 and a load resistor (e.g., a carbon load resistor) 508 are deposited on top of selected ones of the electrodes deposited as part of the electrode layer 504. A transistor (TFT) 510 is built by printing a source electrode 512 and a drain electrode 514 using the same conducting material as for the gas sensor electrode 506. Work function modification layers 516, 518 are selectively printed or deposited directly on substantially only the source and drain electrodes 512, 514 as needed.

A semiconductor layer (the specific material depending on whether the device is for an n-channel or p-channel transistor) 520 is deposited, followed by the gate dielectric 522 and gate contact 524 layer. Also illustrated as part of gas sensor 500 of FIG. 5, is structure for sensor bias 526 (which corresponds to top line 410 or FIG. 4), where the sensor bias is the voltage that drives the sensor. A ground electrode 528 corresponds to the ground 406a of FIG. 4. And elements 530a, 530b correspond to line 414a of FIG. 4 which goes to the TFT 510. Finally contact line 532 can be employed to connect to other TFTs.

In addition although not shown in FIG. 5, connection lines to off the substrate can be provided such as lines 410, 412, 416, 418. The constructed TFT 510 shown here is understood to be generic and may be designed as a p-channel or a n-channel TFT dependent on the materials used, and is also understood to be an inverter TFT as discussed in connection with sensor 400 of FIG. 4. While a single inventor TFT is shown in an embodiment the inverter chain is completed by connecting the source and drain electrodes of one element of the chain to the gate electrode on the next element.

With regard to the gas sensors 400 of FIG. 4 and 500 of FIG. 5, it is noted the construction of these sensors 400, 500 are designed to make it possible to select which resistive gas detection arrangement to print after the metal electrode layer material has already been printed. In this situation an additional printing of the resistive gas detection arrangement can be done after testing to optimize the gas sensors 400, 500.

Figure 6:
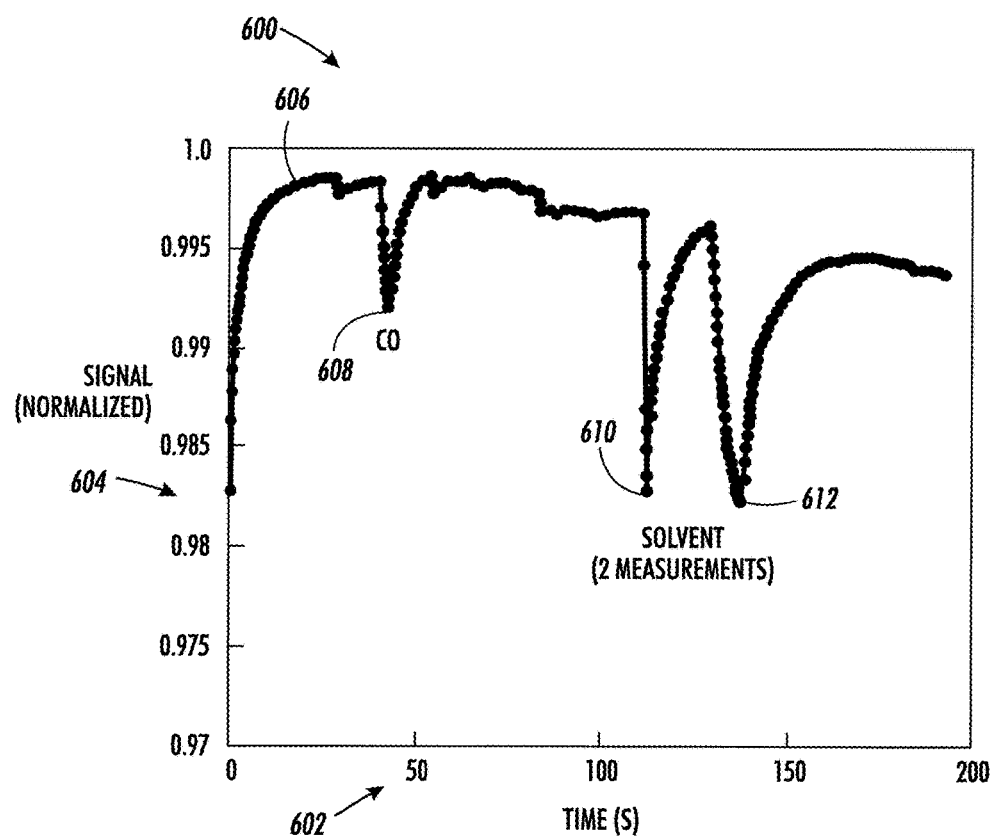
FIG. 6 is a is a graph depicting operational characteristics of the printed resistive gas detection arrangement.

Graph 600 of FIG. 6 plots time (seconds) 602 verses output voltage 604 from the printed resistive gas detection arrangement (e.g., 404, FIG. 4), by graph line trace 606. The graph 600 shows an example of the relative change in input voltage (e.g., to the gain stage 408) 608 when the sensor is exposed to 100-1000 ppm of carbon monoxide (CO) at approximately 29-30 seconds. The voltage is shown to change by approximately 1%. Additional voltage changes 610, 612 occur when the printed resistive gas detection arrangement (e.g., 404 of FIG. 4) is exposed to a volatile organic solvent. The solvent exposure was provided to illustrate a comparison to the CO exposure.

Figure 7:
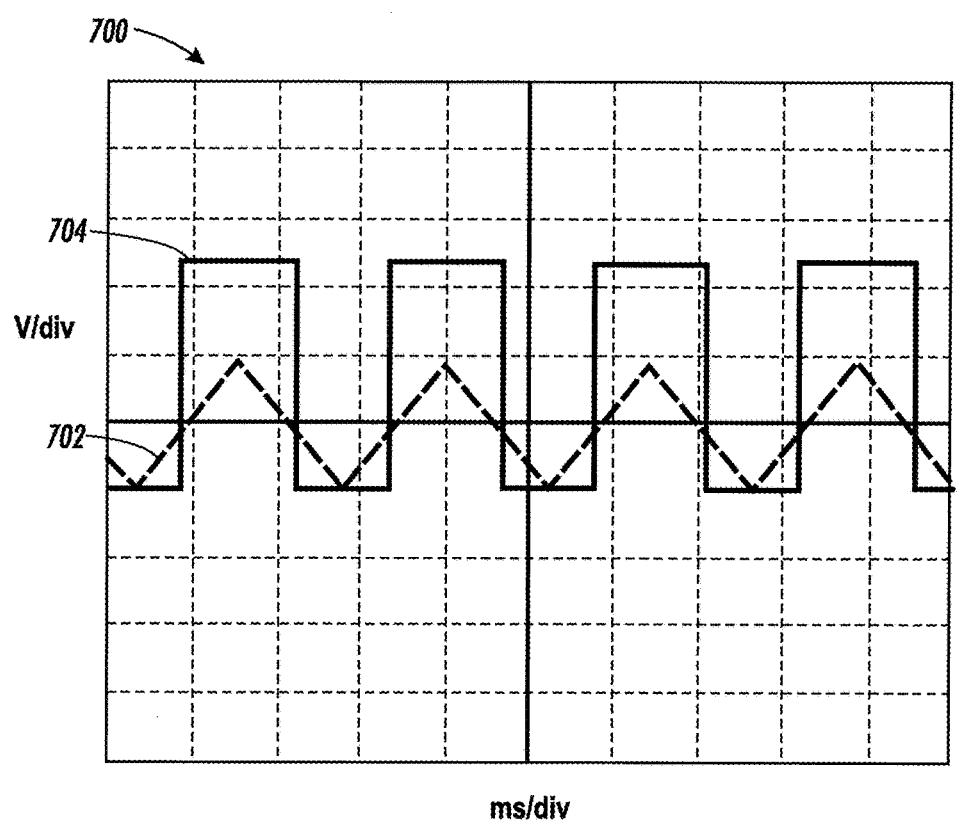
FIG. 7 is a graph comparing waveforms of voltage changes in connection with the present disclosure.

Graph 700 of FIG. 7 includes a voltage ramp signal 702, and a gas presence output signal 704 illustrating the gain stage 408 inverter response to the voltage ramp signal 702, for a device of the present disclosure (e.g., a printed resistive gas sensor 400). There is an approximately 1% change in the resistance of the gas detection arrangement 402 for the specific level of exposure. Hence when the voltage applied via bias line 410 to the printed resistive gas sensor 404 is 20V, and assuming that the load resistor 406 has approximately the same resistance as the gas detection arrangement 404, then the change in input voltage to the gain stage 408 is about 0.1V. With the inverter gain of the gain stage 408 measured to be 240 in this example, the output swing is 24V (i.e., on output line 416), implying that the gain stage (e.g., inverter series) is fully switched.

It is noted the discussed output stage (e.g., 302, 420) is optional. A purpose of the output stage is to couple the relatively high-impedance output of the printed electronics circuit to the indicator. In particular, driving an LED can require higher currents than are easily sourced by conventional circuit designs.

The output stage electronics are selected to operate with the high voltage of the printed electronics. In an embodiment a high-voltage power MOSFET may be used with a Zener diode to connect the output of the printed sensor circuit to the indicator circuit, but other alternative arrangements are possible.

Figure 8:
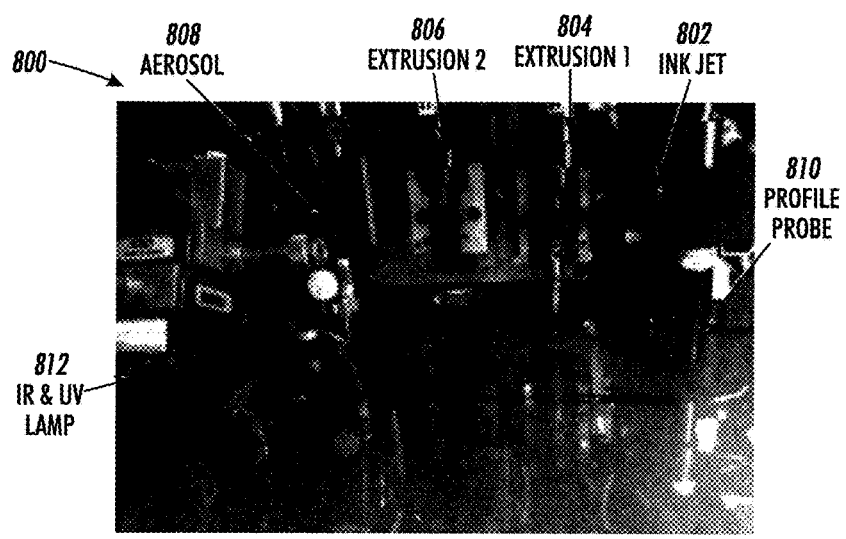
FIG. 8 depicts a printed gas sensor incorporated into an electronic device.

A particular embodiment for the subject matter described above uses 8 different material layers (2 resistors, 2 semiconductors, 2 interface layers, and 2 metal/conductors). Some of the materials are needed in very small quantity, for example the work function modification materials Turning to printing system 800 of FIG. 8, it is noted the printing process used in embodiments employing printing system 800 to generate the gas detection arrangements of the forgoing discussion is an additive process and only the material that is needed is deposited, which saves cost compared to subtractive processes. Further, it is noted the printing system 800 employs a plurality of print heads (e.g., ink jet 802, extrusion1 804, extrusion2 804, aerosol 808) so that multiple materials can be deposited in a single system, such a design saves capital cost and process time. Printing system 800 also includes a profile probe 810 and an infrared (IR) and ultraviolet (UV) lamp arrangement 812.

Turning to electronic device 900, the following discussion will disclose the incorporation of the system including a gas sensor such as in the form of a printed resistive gas detector (sensor) configuration and accompanying optional elements as discussed in connection with FIGS. 1-5 above. The electronic device 900 of FIG. 9 may be an electronic computing and/or communication device such as but not limited to a cell phone, smart phone, laptop, desktop computer, tablet computer, or other such device including electronic circuitry that may expel or generate gases that may be of concern. In this embodiment, electronic device 900 includes a display 902, speaker 904, an input section (e.g., keyboard/voice input) 906, a power source 908, a controller/software area 910, and a printed resistive gas detection configuration 912 in accordance with the present teachings. The foregoing components are held within a body portion 914, which may be comprised of plastic, glass and/or other materials as in known in the art. The gas sensor element of detector 912 in certain embodiments also be placed next to a small opening in the body portion to allow exposure to the ambient and/or sensing the presence of the gas.

The various components discussed in connection with electronic device 900 are for discussion purposes, and it is understood that specific arrangements and configurations and components will vary for particular electronic devices. For example, the display 902 is shown as a specific area in certain devices may cover an entire display area of screen, such as in smart phones, tablets, among other devices. Similarly, the input device area 906 may be generated via software on a display screen and may also be hardware, such as in the form of computer keys, etc. The controller/software area 910 is the intelligence of the electronic device and includes items such as memory storage, central processing units (CPUs) along with other hardware and software that are operated on or by the controller in order to control operations of the other various components. In this design, the printed resistive gas sensor 912 is operationally associated with these components, such as the power area 908 to supply power to the various elements such as discussed in the previous discussions. In this embodiment, the printed gas sensor 912 is provided with an input to the controller/software area 910. This in one instance includes passage/provision of the gas presence signal to the controller/software area 910 which then uses the signal to generate an indicator signal on the display 902 and/or the speaker 904, when a predetermined concentration of gas has been detected. For example, when a predetermined concentration of a particular gas has been sensed by printed gas sensor 912, causing a gas presence signal to be received, the controller 910 generates and forwards data to the display 902 providing a visual warning indicator on the display. Similarly, and or alternatively once such a gas presence signal is provided to controller 910, an output to the speaker 904 is provided that in certain embodiments provide a voice output or other alarm to alert that the undesirable amount of gas has been detected. Thus for device 900 the display 902 and/or the speaker 904 are employed as the gas presence indicator (e.g., 210, 422) discussed in connection with FIGS. 2-5. Also, it is to be understood that when necessary the optional output circuit (e.g., 302, 420) is also incorporated into the electronic device 900.

The power area 908 provides an input to the printed gas sensor 912 that is capable of providing bias voltages to the components such as discussed in connection with FIGS. 1-5.

Figure 9:
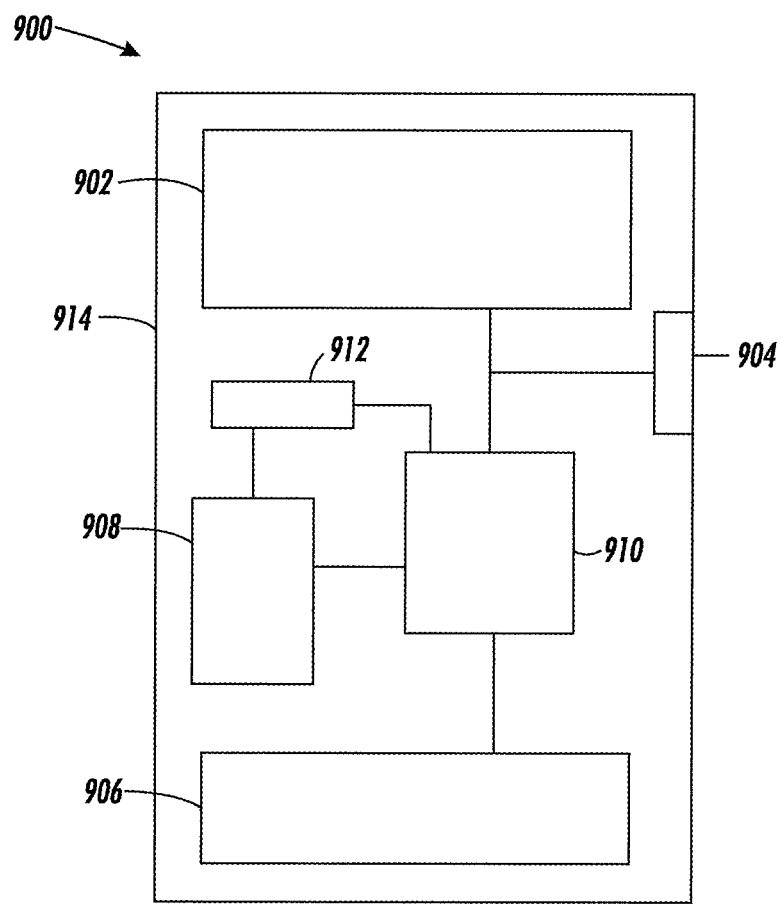
FIG. 9 illustrates a multi head printing device used to manufacture a printed gas detector according to the present disclosure.

In FIG. 9, the printed gas sensor 912 is depicted as separate from the controller/software area 910. It is however to be appreciated that due to the compact nature of such a device, it may be incorporated within the controller/software area 910.

By providing the printed gas sensor 912 incorporated within the electronic device 912, safety is improved in situations where a potential battery fire or other malfunction of the electronic components can be avoided.

There is considerable flexibility in the choice of materials used and in the circuit design in addition to those discussed above. For example, but not being limiting, other printed sensor and load resistor materials could be used, and several known organic semiconductors (e.g. polymers such as polythiophene, small molecules such as pentacene or rubrene and their numerous derivatives) that are appropriate for the TFT inverter or other gain stage circuit may be employed.

Contacts in the present disclosure need not be printed metal. Any conductor, solution-processed, printed or otherwise deposited, can be used, including metal, carbon, conductive polymer.

The printed gas detection arrangement (e.g., 104, 404) can be any printed material that changes resistance with gas concentration. Carbon nanotubes (CNTs) provide high surface area for high sensitivity, but are not required. For example conductive polymers such as PEDOT can be used for gas sensing. CNTs can be functionalized, coated with polymers, or decorated with nanoparticles to enhance sensitivity to different gases and reduce sensitivity to water vapor and other interferents.

Also, as previously mentioned different gain circuit can be used in place of the inverter chain. For example, but not being limiting thereto, a transimpedance amplifier, feedback latch or half latch can be used provide gain.

The calibration supply voltages on the inverters and sensor can be automatically generated with software and a feedback circuit, such as possible in an electronic device such as shown in FIG. 9 (e.g., the controller 910 can detect the amount of voltage being supplied by the power supply 908 to the printed gas sensor 912, and based on the signals from these components can alter the bias voltages accordingly.

The output stage (e.g., 302, 420), which may use conventional electronics, is optional. Further a variety of different output stages may be employed for the disclosed subject matter. For example, without being limiting thereto, any of various comparator circuits and LED driving circuits can be used.

Returning attention to the construction of the gas sensor(s), and more particularly to the TFTs, such as discussed in FIGS. 4 and 5. These may be organic thin film transistors (OTFTs), and may be arranged as a complementary TFT package having a p-type TFT and an n-type TFT in an inverter arrangement, as well as other embodiments having all p-type or all n-type TFTs.

As part of manufacturing such devises it is known to provide a surface work function modifier to improve the operational aspects of the TFTs. For example an energy level for an electrode of pristine silver (Ag) for a p-type TFT may be modified—e.g., to an energy level for modified Ag-F4TCNQ (organic electron acceptor 2,3,5,6-tetrafluoro-7,7,8,8-tetracyanoquinodimethane). The modified energy level for the Ag-F4TCNQ moves to an energy level for a highest occupied molecular orbital (HOMO) of the organic molecules of a p-type semiconductor material. A similar type of modification can be undertaken for an Ag or gold electrode for a n-type TFT where an appropriate surface work function modifier is used to move an energy level towards a lowest occupied molecular orbital (LOMO) of the used n-type semiconductor material. Presently a known manner of providing surface work function modifier layers is to immerse the electrodes and structure within an appropriate bath, which thereafter requires cleaning and other steps to ensure proper layer formation.

With more specific attention the process of making such TFTs according to the present disclosure, attention is now directed to a process of manufacturing a complementary TFT where the p-type TFT includes a surface work function modifier layer, and the n-type TFT does not.

Figure 10:
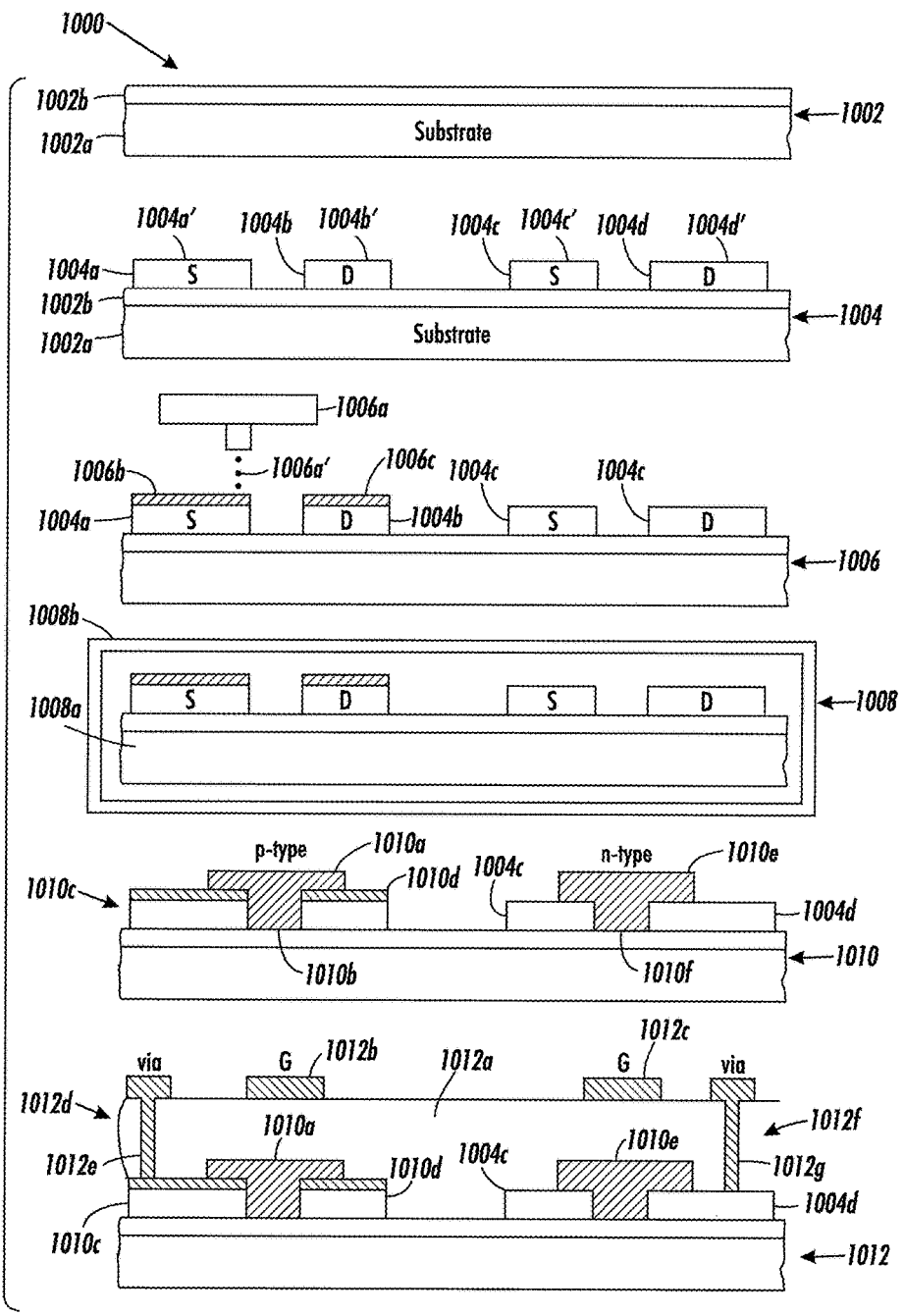
FIG. 10 illustrates processing steps for making a complementary top gate OTFT circuit with selective p-type electrosurface modifications according to the present disclosure.

Turning now to FIG. 10 illustrated are processing steps for a manufacturing method according to the present disclosure.

Process 1000 begins with step 1002 which provides a substrate 1002a and a buffer layer 1002b provided in a manner which is known in the art. In step 1004, source electrode 1004a, and drain electrode 1004b for a p-type OTFT, and source electrode 1004c and drain electrode 1004d for an n-type OTFT are patterned on top of buffer layer 1002b, where source electrode 1004a includes a surface 1004a', drain electrode 1004b includes a surface 1004b', source electrode 1004c includes a surface 1004c', and drain electrode 1004d includes a surface 1004d'.

These electrodes (1004a-1004d) are formed by ink jetting or metal deposition followed by conventionally known photolithography and etching or other known techniques.

Turning to step 1006, to selectively modify electrodes 1004a, 1004b for p-type OTFT devices, provided is a printing system 1006a, configured to print a surface work function modifier material or solution, such as in the form of droplets 1006a', on to surfaces 1004a', 1004b' of the source and drain electrodes 1004a, 1004b for a p-type OTFT. In one embodiment, the surface work function modifier is a F4TCNQ ink or solution, which in an embodiment is formed by dissolving approximately 0.1 weight % F4TCNQ in dichlorobenzene. In an embodiment the printing system 1006a employees a 60 μm to 80 μm nozzle (such as a McroFab nozzle), although it is understood other printing systems and nozzles may be used. In order to maintain a stable fluidic state for the F4TCNQ material the nozzle head is heated and maintained at approximately 100° C. to 60° C., and more particularly 50° C. during the ink-jetting (or printing) of the droplets. For sufficient reaction between F4TCNQ with the surfaces 1004a', 1004b' of the Ag electrodes 1004a, 1004b, multiple droplets are applied to the p-type electrodes 1004a, 1004b. Thus, the printing operations selectively deposit a layer of the surface work function modifier (e.g., F4TCNQ) 1006b, 1006c on the surfaces 1004a', 1004b' of the electrodes 1004a, 1004b. The droplet volume of the surface work function modifier (e.g., F4TCNQ) material is approximately between 100 pL/mm$^2$ to 10 nL/mm$^2$ or more particularly 200 pL/mm$^2$ to 3000 pL/mm$^2$. Where droplet volume is the total volume of individual droplets deposited on both of the surfaces of the the source electrode and drain electrode for a particular p-type OTFT. The droplets being deposited on an electrode surface area (including the source electrode and drain electrode for the p-type OTFT) of approximately between 100 pL/mm$^2$ to 10 nL/mm$^2$ or more particularly 200 pL/mm$^2$ to 3000 pL/mm$^2$.

It is noted that distinct from previously employed processes the present process of FIG. 10 (and those of FIGS. 11 and 12) continues without the use or requirement of immersion or submersion of the electrodes into a bath of a surface work function modifier solution. Also not required is the applying of a solvent rinse to remove unwanted surface work function modifier solution. This solvent rinsing or other cleaning steps are not needed as the present processes do not use the step of immersion, but rather used precise selective printing of the energy surface modification material onto surfaces of the desired electrodes. It is also noted that all of the electrodes (1004a-1004d) maybe formed in the same step, unlike what is required in existing processes.

With continuing attention to process 1000, following the jetting of the first surface work function modifier (e.g., F4TCNQ), as shown in step 1008, sample 1008a (which includes substrate 1002a, buffer layer 1002b, electrodes 1004a-1004d, and the surface work function modified layers 1006b, 1006c) is provided to an heater (e.g., a vacuum oven) 1008b where in one embodiment the sample 1008a is annealed at about 120° C. for approximately 5 minutes. This heating (i.e., after the ink jetting or printing etc.) acts to remove undesirable solvents that are otherwise present due to previous manufacturing steps. The described operations act to modify the surface energy level such as discussed in connection with FIG. 1. Achievement of energy level alignment is useful for appropriate ohmic contact. Surface modifications reduce the charge injection barrier at the organic molecules/metal interfaces. In one example the modification of ink-jet or printed silver (Ag) electrodes with organic electron acceptor 2,3,5,6-tetrafluoro-7,7,8,8-tetracyanoquinodimethane (F4TCNQ) produce charge transfer complexes with silver to alter the work function from 4.70 eV to 5.15 eV. This type of modification improves energy level alignment between the modified electrode and the HOMO of the p-type organic semiconductor.

Following the heating process, as shown in step 1010, a p-type semiconductor material 1010a is jetted or printed into the channel region 1010b. It is noted printing of the p-type material 1010a also extends over onto a portion of an upper surface of modified source electrode 1010c and modified drain electrode 1010d for the p-type OTFT. Similarly, in step 1010, n-type material 1010e is jetted (or printed) into channel 1010f. Further, some of the n-type semiconductor material 1010e extends onto surfaces of the unmodified source electrode 1004c and the drain electrode 1004d. In other words, these electrodes are of the same metal structure as in step 1004, whereas the electrodes for the p-type OTFT in step 1010 have been modified from the electrode structure composition of the electrodes 1004a and 1004b of step 1004.

Thereafter, in step 1012, a dielectric layer 1012a is provided over the electrodes 1010c, 1010d, 1004c, 1004d, as well as the p-type semiconductor material 1010a, and the n-type semiconductor material 1010e. Thereafter, gate electrodes 1012b and gate electrodes 1012c are printed on the surface of dielectric layer 1012a. In further processing, via 1012d is formed in dielectric layer 1012a for contact with the modified source electrode 1010c and thereafter a conductive material 1012e is provided for a pathway for the modified source electrode 1010c to the surface of dielectric layer 1012a. Similarly, a via 1012f is formed in the dielectric layer 1012a to the unmodified drain electrode 1004d and a conductive material 1012g is provided in the via to form a contact portion to the upper surface of dielectric layer 1012a.

The fabrication process shown in FIG. 10 can apply to other printed source and drain metal materials, such as but not limited to copper or nickel, and to source and drain metals patterned by vacuum deposition and conventional photolithography.

While F4TCNQ is a surface work function modifier which may be used in the process steps related to FIG. 10, it is understood however other dipolar SAM materials capable of surface work function modification are known and may be used dependent on the organic semiconductors that are used to form the complementary OTFT. Such surface work function modifiers for p-type semiconductors include but are not limited to thiol-based SAMs including but not limited to thiophenol, 4-fluorothiophenol, and pentafluorothiophenol. The disclosure also applies to other advantaged combinations of printable surface work function modifiers and organic semiconductors that may be synthesized in the future.

In the present embodiments the p-type and n-type semiconductor materials may include those known in the art which are appropriate for the present concepts.

Figure 11:
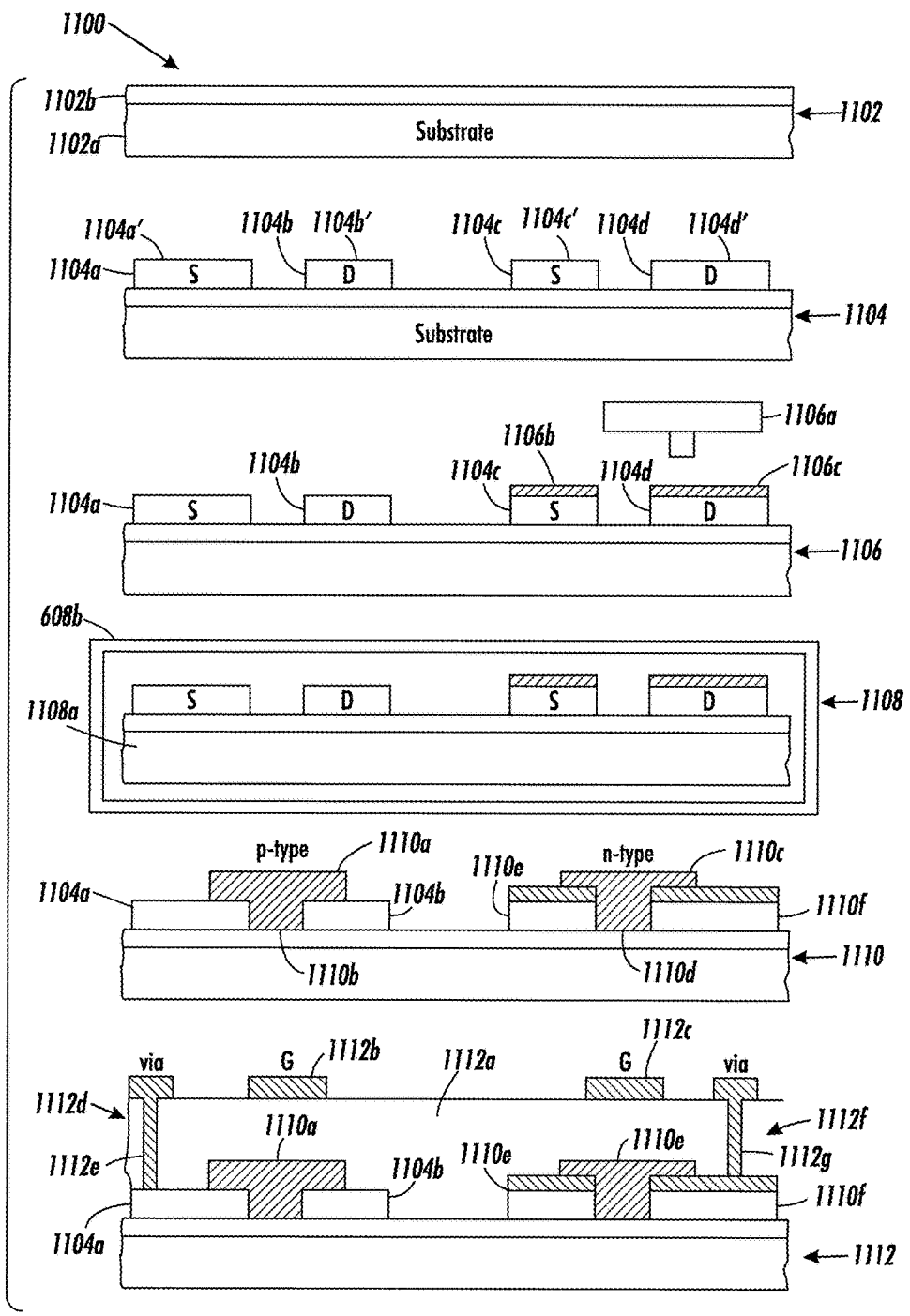
FIG. 11 depicts processing steps for making a complementary top gate circuit with selective n-type electrode surface modifications according to the present disclosure.

Turning now to FIG. 11, illustrated is a process 1100 wherein the modified electrodes are the electrodes related to the n-type OTFT. Similar to FIG. 10, in step 1102, a substrate 1102a and a buffer layer 1102b are provided.

Then in step 1104, a source electrode 1104a, drain electrode 1104b for a p-type OTFT are formed, along with a source electrode 1104c and a drain electrode 1104d for a n-type OTFT. These electrodes can be made by ink jetting (or printing) or metal deposition followed by conventional photolithography and etching or in other manners known in the art. It is also noted that source electrode 1104a includes an upper surface 1104a', drain electrode 1104b includes an upper surface 1104b', source electrode 1104c includes an upper surface 1104c', and drain electrode 1104d includes an upper surface 1104d'.

Thereafter, in step 1106, provided is a printing system 1106a, which is used to ink jet or print another (e.g., second) surface work function modifier material or solution 1106b, 1106c onto upper surfaces of source electrode 1104c and drain electrode 1104d. The surface work function modifier for the n-type OTFT may be selected from, but is not limited to methoxythiophenol, 4-methylthiophenol, 4-aminothiophenol, and 4-nitrothiophenol nitrothiophenol. In addition to the foregoing, for some choices of source and drain metal materials, or organic semiconductors, a printed surface work function modifier (dipolar SAM), such as but not limited to polyethylenimine ethoxylated (PEIE), on the n-channel OTFT can also be used.

The droplet volume of the surface work function modifier material for the n-type OTFT is approximately between 100 pL/mm$^2$ to 10 nL/mm$^2$ or more particularly 200 pL/mm$^2$ to 3000 pL/mm$^2$. Where droplet volume is the total volume of individual droplets deposited on both of the surfaces of the the source electrode and drain electrode for a particular n-type OTFT. The droplets being deposited on an electrode surface area (including the source electrode and drain electrode for the n-type OTFT) of approximately between 100 pL/mm$^2$ to 10 nL/mm$^2$ or more particularly 200 pL/mm$^2$ to 3000 pL/mm$^2$.

Also, the nozzle of the printing system for depositing the surface work function modifier for the n-type OTFT is able to operate at room temperature without additional heating.

Following the actions of step 1106 the process moves to step 1108, where the sample 1108a (which includes substrate 1102a, buffer layer 1102b, electrodes 1104a, 1104b, 1104c, 1104d, layer 1106b and layer 1106c) is placed in an oven (e.g., a vacuum oven) 1108b at 120° C. for approximately 5 minutes to anneal. This heating (i.e., after the ink jetting or printing etc.) acts to remove undesirable solvents that are otherwise present due to previous manufacturing steps. The described operations act to modify the surface energy level such as discussed in connection with FIG. 1.

Thereafter, in step 1110, a p-type semiconductor material 1110a is printed or otherwise deposited into a channel 1110b between unmodified source electrode 1104a and unmodified drain electrode 1104b. and a n-type semiconductor material or ink 1110c is deposited within a channel 1110d between modified source electrode 1110e and modified drain electrode 1110f.

Next, in step 1112, a dielectric layer 1112a is deposited over the electrodes 1104a, 1104b, 1110e, 1110f, as well as the p-type semiconductor material 1110a and 1110c. On a surface of the dielectric material, gates 1112b and 1112c are formed. Further, a via 1112d is formed from the surface of the dielectric material 1112a to the unmodified source electrode 1104a which is then filled with a conductive material 1112e. Similarly, a via 1112f is formed in the dielectric material 1112a from the modified drain electrode 1110f to the surface of the dielectric layer 1112a. Thereafter, a conductive material 1112g fills the via 1112f forming a conductive path from the modified drain electrode 1110f to the surface of the dielectric layer 1112a.

Figure 12:
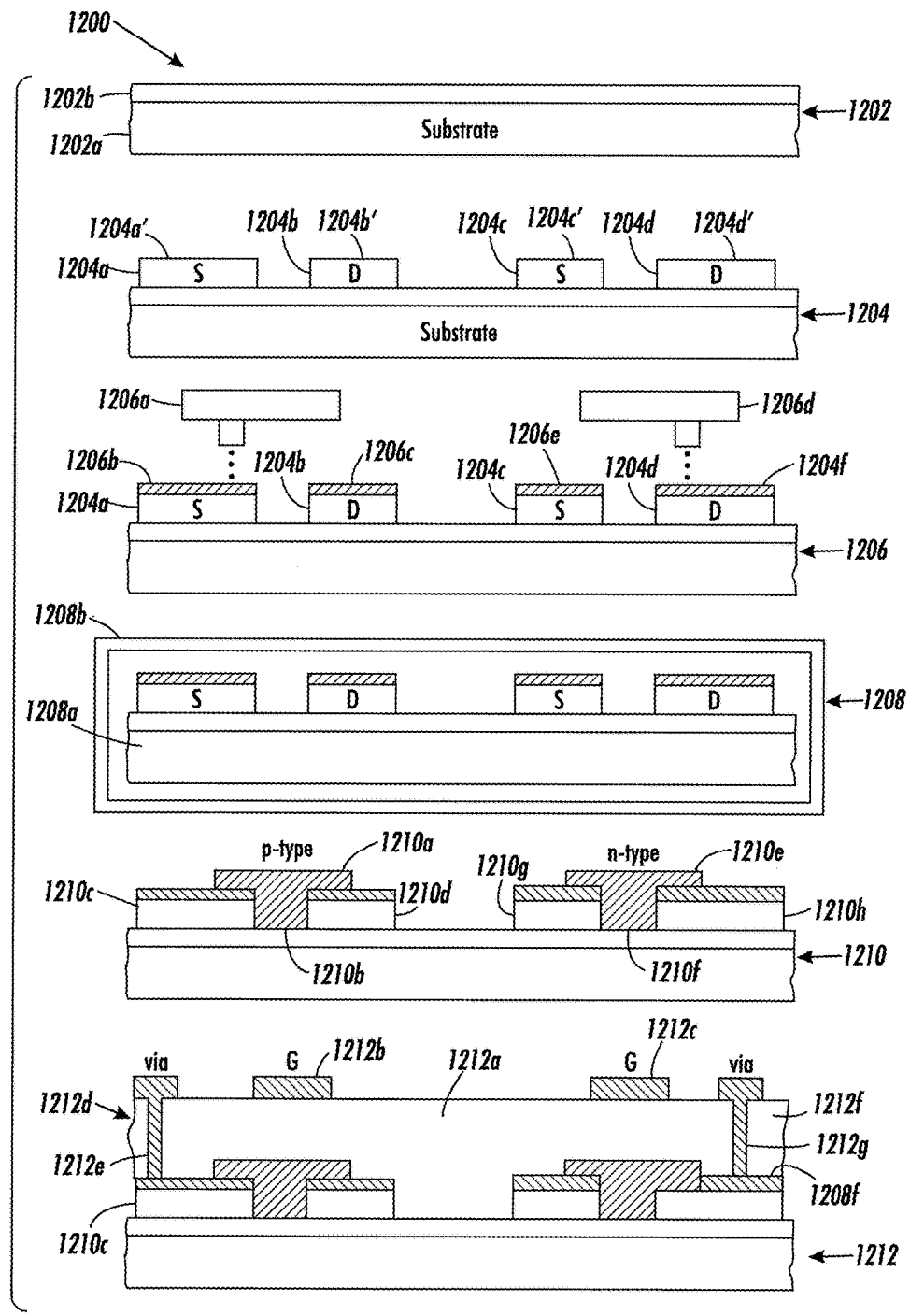
FIG. 12 illustrates processing steps for making a complementary top gate OTFT circuit with selective p-type electrode surface modifications and n-type electrode surface modifications according to the present disclosure.

Turning to FIG. 12, illustrated are processing steps 1200 used to form a complementary top gate OTFT having the energy levels of both the electrodes for the p-type OTFT and the n-type OTFT modified.

Step 1202 is similar to the previous embodiments where a substrate 1202a and a buffer layer 1202b are provided. Thereafter, as shown in step 1204, a source electrode 1204a and drain electrode 1204b for a p-type OTFT are formed, along with a source electrode 1204c and electrode 1204d for a n-type OTFT. Also, source electrode 1204a includes a surface 1204a', drain electrode 1204b includes a surface 1204b', source electrode 1204c includes a surface 1204c', and the drain electrode 1204d includes a surface 1204d'.

It has been determined by the inventors that it is possible to modify electrodes for both the p-type OTFT and the n-type OTFT. In view of this in step 1206 a printing system 1206a is operated to print a surface work function modifier, as layer 1206b on the source electrode 1204a, and a layer 1206c on the drain electrode 1204b. In certain embodiments the nozzle of the printing system 1206a is heated to maintain certain types of surface work function modifier material in a fluid state. Further in the processing step 1206, a printer system 1206d (which may be part of or separate from the printing system 1206a) prints an other energy surface work function modifier as a layer 1206e on source electrode 1204c and a layer 1206f on drain electrode 1204d.

Turning to step 1208, the sample 1208a of the arrangement created by step 1206 is placed in an oven (e.g., a vacuum oven) 1208b to anneal the sample 1208a, as in the preceeding embodiments. This heating (i.e., after the ink jetting or printing etc.) acts to remove undesirable solvents that are otherwise present due to previous manufacturing steps. The described operations act to modify the surface energy level such as discussed in connection with FIG. 1.

Next in step 1210, a p-type semiconductor material 1210a is printed in a channel 1210b between modified source electrode 1208c and modified drain electrode 1208d. Similarly, an n-type semiconductor material 1210c is printed in a channel 1210d between modified source electrode 1208e and a modified drain electrode 1208f.

Following these operations, the process moves to step 1212, where a dielectric layer 12012a is printed or deposited over the modified electrodes 1208c, 1208d, 1208e, and 1208f, as well as over the p-type semiconductor material 1210a and n-type semiconductor material 1210c. Thereafter, gates 1212b and 1212c are printed on a surface of the dielectric layer 1212a. Then via or opening 1212d is formed from the surface of the dielectric layer 1212a to the modified source electrode 1208c. Thereafter, a conductive material 1212e is provided to form a conductive connection from the source electrode 1208c to the surface of dielectric layer 1212a. In a similar manner, via or opening 1212f is formed in the dielectric layer 1212a to the modified drain electrode 1208f. Thereafter, a conductive material 1212g is provided to form a conductive path from the modified drain electrode 1208f to the surface of the dielectric layer 1212a.

Figure 13:
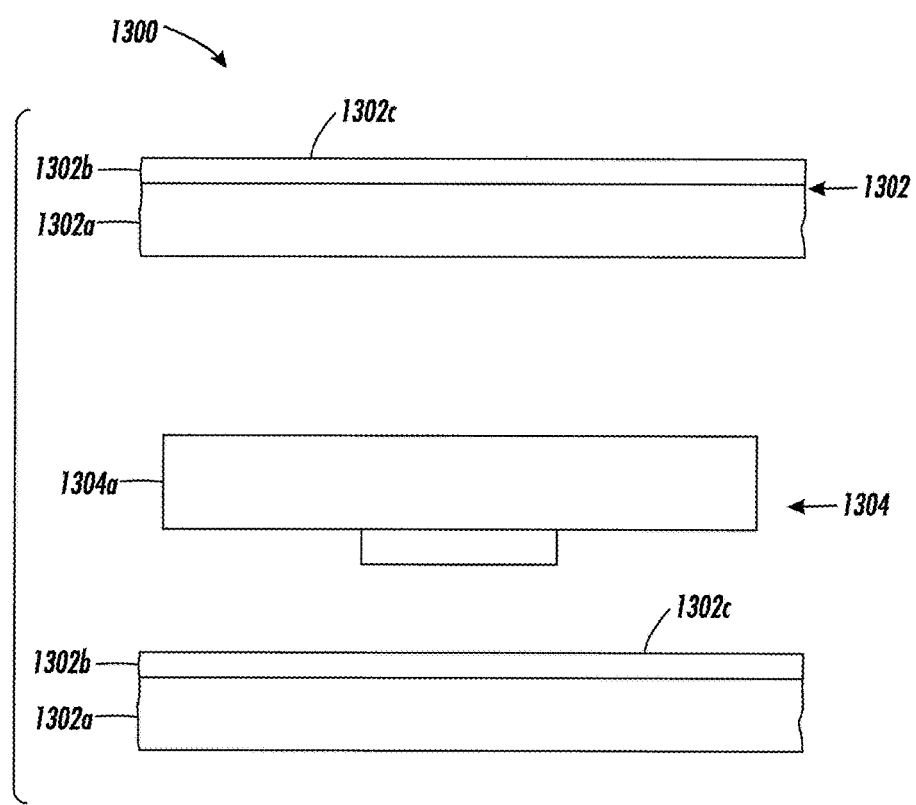
FIG. 13 illustrates a modification of the buffer layer optionally implemented in the processing steps shown in FIGS. 10, 11.

Turning to FIG. 13, illustrated is a process 1300 which optionally is provided between steps 1002 and 1004 of FIGS. 10, 1102 and 1104 of FIG. 11, and 1202 and 1204 of FIG. 12, or at another step as appropriate. In particular, illustrated is substrate 1302a, similar to the substrates 1002a, 1102a, and 1202a, and buffer layer 1302b, similar to the buffer layers 1002b, 1102b, and 1202b. As in the previous arrangements buffer layer 1302b includes a surface which is identified herein as surface 1302c.

In step 1304, surface roughening device 1304a is provided in operational association with the surface 1302c of buffer layer 1302b. The roughening device 1304a is used to provide a roughening to the surface 1302c prior to the further steps in the process as described in FIGS. 10, 11, and 12. Roughening step 1304 may be accomplished by application of an argon plasma (Ar) or oxygen (O) treatment, such as by use of a roughening device (e.g., an argon or oxygen plasma generating device) 1304a. Alternatively the roughening device may be any other device or arrangement which will provide appropriate roughening of the buffer surface. For the argon roughening the surface treatment includes providing Ar at 40-200 m Torr, 100 W for approximately 30 seconds.

The roughing of surface 1302c of buffer layer 1302b is undertaken to insure an appropriate contact during the depositing of the p-type semiconductor material and the n-type semiconductor material. For example, the processes which are used to form the electrodes may leave the buffer layer surfaces (and/or electrodes) somewhat hydrophobic which will limit the wicking or spreading of the p-type and/or n-type semiconductor material. The roughening operations allows for a more complete speading of the semiconductor material which in turn provides a stronger interface between the buffer layer (and/or electrodes) and the semiconductor material.

Figure 14:
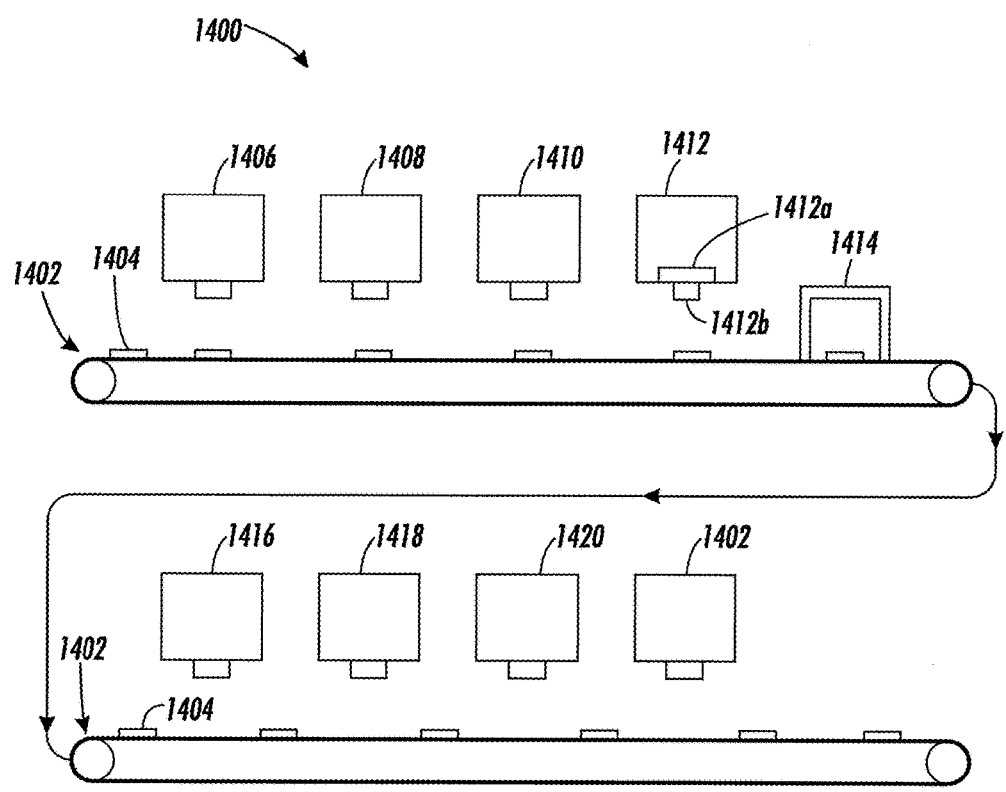
FIG. 14 illustrates a manufacturing system which permits a role-to-role manufacture of the complementary top gate OTFT circuits of FIGS. 10, 11, 12 and the processing step of FIG. 13.

Turning to FIG. 14 illustrated is a roll-to-roll processing system 1400 designed to form complementary top-gate OTFTs. Included is a roll-to-roll conveyor 1402 having the appropriate hardware and arrangement to move a substrate through processing steps as defined in the forgoing disclosure. The conveyor 1402 is designed to carry substrates 1404 through the processing operations.

Initially, a buffer printing system 1406 operates to deposit and otherwise form a buffer layer on the substrate 1404. Alternatively the substrate may be prefabricated with the buffer layer. Next, a roughening station 1408 is optionally provided to roughen a surface of the buffer layer. An electrode generating station 1410 functions to deposit and otherwise form electrodes on to the surface of the buffer layer. Further included is an energy surface modification system 1412 which is employed to print or otherwise deposit surface work function modifier material for one of or both of the p-type OTFT abd the n-type OTFT, selectively on the electrodes. It is noted that in at least some embodiments a heater 1412a is optionally associated with a nozzle 1412b of system 1412, in situations where the first and/or second surface work function modifiers are of a solution that requires a certain temperature to be applied in order to maintain the surface work function modifier in a flowing or liquid state.

Further located as part of the roll-to-roll system 1400, is a heater or oven 1414, such as but not limited to a vacuum oven configured for annealing operation. Following the heating operation the substrates which are being processed are moved to a dielectric forming station 1416, where a dielectric layer is printed or deposited over the material previously formed on the substrates. Next a metal depositing station 1416 is configured to deposit gate electrodes in accordance with the previously discussed processing steps. After the foregoing the system 1400 moves the substrates and layers formed thereon to via (or opening) forming station 1420 which, maybe a laser, mechanical drill, etc., which to form vias or openings in the dielectric layer. Finally, a conductive material depositing system 1422, such as a printer is provided to fill the previously formed vias or openings.

It will be appreciated that variants of the above-disclosed and other features and functions, or alternatives thereof, may be combined into many other different systems or applications. Various presently unforeseen or unanticipated alternatives, modifications, variations or improvements therein may be subsequently made by those skilled in the art which are also intended to be encompassed by the following claims.

What is claimed is:
1. A system including a gas sensor comprising:
a flexible substrate;
a printed resistive gas detection arrangement including a resistive gas sensor material designed to alter its resistance characteristics upon coming into contact with a gas to be sensed;
a printed bias input line arrangement configured to supply a bias voltage to the printed resistive gas detection arrangement;
a printed load resistive element positioned to form a voltage divider network with the printed resistive gas detection arrangement;

a printed gain stage to receive the supply voltage of the voltage divider, the printed gain stage including a printed thin film transistor which includes a surface work function modifier on at least certain electrodes, wherein the surface work function modifier modifies the surface work function of the certain electrodes; and a printed output line in operational association with the output portion of the printed gain stage.

2. The system according to claim 1 further including a gas presence indicator, configured to indicate a presence of a sensed gas.

3. The system according to claim 1 further including an output stage configured to couple output of the gain stage to a gas presence indicator.

4. The system according to claim 1 further including, (i) a wireless transmitter configured to receive output from at least one of the printed gain stage and an output stage associated with the printed gain stage, and (ii) a gas presence indicator having a wireless receiver to receive a gas presence signal from the wireless transmitter.

5. The system according to claim 1 wherein the printed gain stage includes at least one of a single inverter and a series of connected inverters.

6. The system according to claim 1 wherein the printed gain stage includes at least one of a transimpedance amplifier, feedback latch and a half latch.

7. The system according to claim 1 wherein at least some of the printed portions are part of a printed conductive layer formed by use of at least one of a metal material, a carbon material and a conductive polymer material.

8. The system according to claim 1 wherein the printed resistive gas detection arrangement is configured with carbon nanotubes.

9. The system according to claim 8 wherein the carbon nanotubes are at least one of functionalized carbon nanotubes, carbon nanotubes coated with polymers, and carbon nanotubes are decorated with nanoparticles.

10. The system according to claim 1 wherein the supply voltages supplied to the printed gain stage and the printed resistive gas detection arrangement are calibrated by software control operations and a feedback circuit.

11. The system according to claim 1 wherein the substrate, the printed conductive layer, the printed resistive gas detection arrangement, the printed bias input line, the printed load resistive element, the printed supply line, the printed gain stage, and the printed output line are formed to be flexible and compact.

12. The system according to claim 1 wherein the printed gas detection arrangement includes more than a single printed gas detector, each printed gas detector of the printed gas detection arrangement configured to sense a different gas.

13. The system according to claim 1 wherein the substrate, the printed conductive layer, the printed resistive gas detection arrangement, the printed bias input line, the printed load resistive element, the printed supply line, the printed gain stage, and the printed output line are arranged as part of at least one of an electronic computing device and an electronic communication device, and wherein the printed output line is in operational association with a visual display or speaker of the at least electronic computing device and electronic communication device.

14. A system including a gas sensor comprising:
a flexible substrate;
a flexible conductive layer formed in a predetermined pattern;

a printed resistive gas sensor configuration carried at least partially on the conductive layer including (i) a printed resistive gas detection arrangement including a resistive gas sensor material designed to alter its resistance characteristics upon coming into contact with a gas to be sensed, the printed resistive gas detection arrangement operationally associated with at least a portion of the printed gas detection arrangement printed onto a portion of the conductive layer and including a bias voltage input area, (ii) a printed bias input line arrangement, of the conductive layer, configured to supply a bias voltage to the bias voltage input area of the printed resistive gas detection arrangement, (iii) a printed load resistive element positioned to form a voltage divider network with the printed resistive gas detection arrangement, wherein at least a portion of the printed load resistive element is printed onto a portion of the conductive layer and including to a ground line of the conductive layer, (iv) a printed supply line, of the conductive layer, configured to supply a voltage in accordance with the voltage divider; and a printed gain stage including an output portion and an input portion and configured to receive the supply voltage from the voltage divider at its input portion, and configured for its output portion to be in operational association with an output line of the conductive layer, the printed gain stage including a printed thin film transistor which includes a surface work function modifier on at least certain electrodes, wherein the surface work function modifier modifies the surface work function of the certain electrodes.

15. The system according to claim 14 wherein the substrate, the printed conductive layer, the printed resistive gas detection arrangement, the printed bias input line, the printed load resistive element, the printed supply line, the printed gain stage, and the printed output line are arranged as part of at least one of an electronic computing device and an electronic communication device, and wherein the printed output line is in operational association with a visual display or speaker of the at least electronic computing device and electronic communication device.

16. A method for forming a system including a gas sensor comprising:
providing a flexible substrate;
printing a resistive gas detection arrangement including a resistive gas sensor material designed to alter its resistance characteristics upon coming into contact with a gas to be sensed;
printing a bias input line arrangement configured to supply a bias voltage to the printed resistive gas detection arrangement;
printing a load resistive element positioned to form a voltage divider network with the printed resistive gas detection arrangement;
printing a supply line configured to provide a supply voltage in accordance with the voltage divider;
printing a gain stage to receive the supply voltage of the voltage divider, wherein the printing of the gain stage includes printing a thin film transistor which includes printing a surface work function modifier on at least certain electrodes and processing the surface work function modifier to modify the surface work function of the certain electrodes;
printing a gain stage bias input line arrangement configured to supply a bias voltage to the gain stage; and
printing an output line in operational association with the output portion of the printed gain stage.

17. The method according to claim 16 wherein the printing steps are additive processes and only material that is needed to print the gas sensor is deposited.

18. The method according to claim 16 wherein the printing steps are undertaken using a printing system having multiple print heads, and a plurality of materials are deposited by the same printing system, wherein the printing materials include at least resistive material, semiconductor material, interface layer material, and conductive material.

* * * * *